Figure 1:
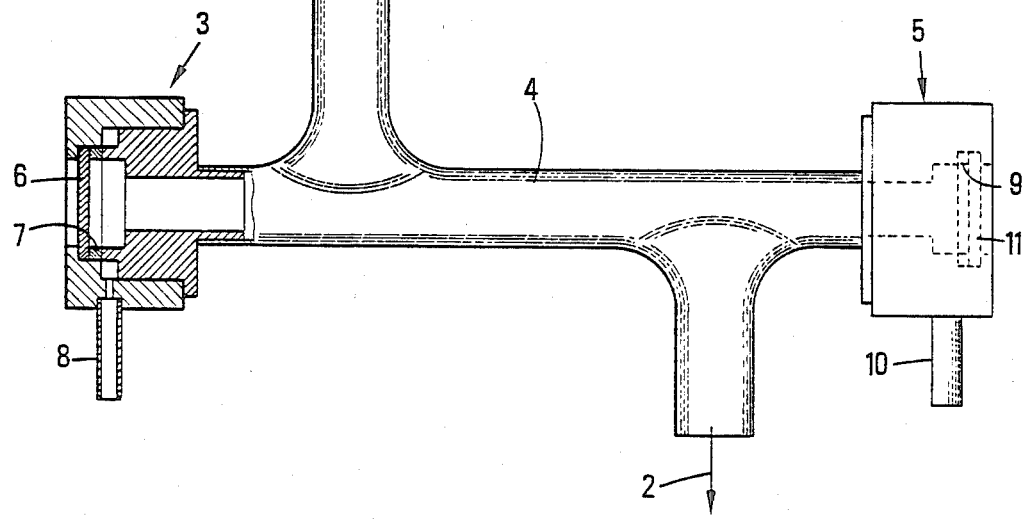

United States Patent [19]

Degobert et al.

[11] Patent Number: 4,796,590
[45] Date of Patent: Jan. 10, 1989

[54] RAPID-RESPONSE METHOD AND DEVICES FOR DETECTION OF POOR COMBUSTION

[75] Inventors: Paul Degobert, Rueil-Malmaison; Emmanuel Goldenberg, Poissy; Yvon Nadaud, Saint-Ouent; Michel Molinier, St. Cloud, all of France

[73] Assignee: Institut Francais du Petrole, Rueil-Malmaison, France

[21] Appl. No.: 802,723

[22] Filed: Nov. 29, 1985

Related U.S. Application Data

[63] Continuation of Ser. No. 534,650, Sep. 22, 1983, abandoned.

[30] Foreign Application Priority Data

Sep. 22, 1982 [FR] France .................. 82 16075

[51] Int. Cl.⁴ .................................. F02D 41/14
[52] U.S. Cl. ............................ 123/489; 123/406; 123/571; 250/373
[58] Field of Search ........... 123/489, 440, 571, 494, 123/406; 250/372, 373; 60/276, 285; 431/76

[56] References Cited

U.S. PATENT DOCUMENTS

| | | | |
|---|---|---|---|
| 2,764,692 | 9/1956 | Millek | 250/373 |
| 2,974,226 | 3/1961 | Fisher | 250/372 |
| 3,205,359 | 9/1965 | Giuffrida | 250/372 |
| 3,362,387 | 1/1968 | Neumann | 60/276 |
| 3,384,746 | 5/1968 | Benz et al. | 250/43.5 |
| 3,630,072 | 12/1971 | Traver | 73/23 |
| 3,751,167 | 8/1973 | Claus | 250/373 |
| 3,999,383 | 12/1976 | Hanaoka | 60/277 |

FOREIGN PATENT DOCUMENTS

| | | | |
|---|---|---|---|
| 1547332 | 10/1969 | Fed. Rep. of Germany | 250/373 |
| 2247451 | 9/1972 | Fed. Rep. of Germany | |

OTHER PUBLICATIONS

"A Novel Gas Analyzer for $SO_2$, NO, and $NO_2$ in Stack Equipment", by Ito et al; Proceedings ICO Conference, Tokyo, 1974.

U. Kiencke et al., "Digitale Regelung des Brennstoffgemisches von Otto–Motoren mit dem Mikrocomputer", Regelungstechnik, vol. 28, pp. 16–21, Jan. 1, 1980.

Primary Examiner—Andrew M. Dolinar
Attorney, Agent, or Firm—Antonelli, Terry & Wands

[57] ABSTRACT

A method of regulating combustion by rapid-response monitoring of the gaseous effluents leaving a combustion chamber, especially the chamber of an internal-combustion engine, includes the steps of emitting ultraviolet radiation to a zone of small volume traversed by at least part of the gaseous effluents leaving the combustion chamber; receiving at least part of the ultraviolet radiation which has passed through this zone; measuring the degree to which the ultraviolet radiation has been absorbed by a chemical compound contained in the gaseous effluents; and governing at least one parameter influencing combustion within the combustion chamber as a function of the degree of absorption.

15 Claims, 2 Drawing Sheets

RAPID-RESPONSE METHOD AND DEVICES FOR DETECTION OF POOR COMBUSTION

This is a continuation of application Ser. No. 534,650 filed Sept. 22, 1983, now abandoned.

The present invention relates to a method and a rapid-response device for detecting the quality of combustion, and enabling at least one parameter affecting combustion to be regulated and, in particular, the automatic regulation of the richness of the air-fuel mixture and/or the recycling rate of exhaust gases and/or the ignition of a controlled-ignition engine.

More particularly, the invention relates to a rapid-response device that is adapted to be used in the exhaust pipes of internal-combustion engines, which device ensures electronic regulation of the richness of the air-fuel mixture, of the recycling rate of the exhaust gases, and of the ignition in the case of a controlled-ignition engine.

The prior art can be illustrated by U.S. Pat. Nos. 3,362,387, 3,384,746, 3,630,072 and 3,999,383; by German Patent Application No. 2,247,451, and by the article by U. Kiencke, et al. entitled "Digitale Regelung des Brennstoffgemisches von Otto-Motoren mit dem Mikrocomputer," published Jan. 1, 1980 in the journal "Regelungstechnik," Vol. 28, pages 16–21.

One essential goal of this invention is to detect poor combustion of the air-fuel mixture in an engine, whether this poor combustion is due to delayed or incomplete combustion or whether it results from a fuel-poor air-fuel mixture, overdilution of the air-fuel mixture by the exhaust gases, etc.

This goal is achieved according to the invention by measuring, in at least part of the engine's effluent gases, a parameter which can be directly associated with the combustion quality of the air-fuel mixture, particularly, when a poor air-fuel mixture is used, when the fuel-air mixture is strongly diluted by recycling the exhaust gases, or in the case of knocking of the engine.

In an internal-combustion engine, the response time can be minimized by making the measurement in the immediate vicinity of the exhaust orifice of each cylinder.

It is advantageous to use aromatic compounds (benzene, toluene, etc.) contained in the gasoline as "tracers" characterizing poor combustion, whereby an increased level of these compounds in the exhaust gases reveals imperfect combustion.

These aromatic compounds have the particular property of absorbing ultraviolet radiation, and this property is exploited in the method according to the invention.

An advantage of these aromatic compounds is that they are already present in a great number of fuels, except in the alcohol and thus it is generally not useful to add other compounds to the air-fuel mixture.

The amount of aromatic compounds of these fuels typically varies between 10 and 50%. The invention can be used even if the amount of the aromatic compound is outside this range, for instance, even if this amount is about 1%.

The addition of other compounds absorbing ultraviolet radiation and normally destroyed by combustion to the fuel or to the combustion air before entry into the combustion chamber is also within the scope of the invention, since the presence of or increase in the level of these compounds in the exhaust gases also reveals poor combustion.

These other components are, for example, compounds with linear or cyclic chromophore groups, in particular, conjugated dienes and polyenes, $\alpha$-diketones or unsaturated $\alpha,\beta$-aldehydes or ketones, conjugated carbonyl or dicarbonyl polyenes, conjungated polyynes or poly(enesynes) groups, or nitrogen compounds, etc., with double conjugated bonds.

Of course, the addition of compounds reacting to a greater or lesser degree upon combustion in connection with combustion quality and of which at least one reaction product absorbs ultraviolet radiation will not depart from the scope of the present invention since the presence, absence, increase, or decrease of this substance in the exhaust gases enables combustion quality to be evaluated. Thus, it is possible to introduce into the combustion chamber intake a compound which supplies by combustion a substance absorbing ultraviolet radiation when combustion is of satisfactory quality and does not supply such a substance or supplies it in small quantities, when combustion is poor.

The reverse case can also be envisaged in the scope of the present invention. Of course, the choice of compound will be determined as a function of the characteristics of the fuel and/or comburent used.

The method employed to regulate combustion by rapid-response control of the gaseous effluents of a combustion chamber is characterized by emission of ultraviolet radiation to a zone of small volume traversed by at least part of the effluents as they leave the combustion chamber, reception of at least part of the ultraviolet radiation which has passed through this zone, and measurement of the degree to which this ultraviolet radiation has been absorbed by a chemical compound contained in the gaseous effluents and by regulating at least one parameter which influences combustion as a function of said degree of absorption.

It is advantageous to measure the variation of the degree to which the ultraviolet radiation has been absorbed by the chemical compound.

In its application to automatic combustion control in an internal-combustion engine, the method, according to the invention, is characterized by controlling the richness of the mixture entering the engine and/or the recycling rate of the exhaust gases and/or the ignition advance as a function of the degree to which ultraviolet radiation, measured in the exhaust gases, has been absorbed.

A device according to the invention comprises, in combination, a first optical system emitting ultraviolet radiation to a zone of small volume traversed by the effluents as the effluents leave the combustion chamber, a second optical system separated from the first by the zone, the second optical system being disposed such as to receive at least part of the ultraviolet radiation which has traversed the zone and being associated with an element measuring absorption of the ultraviolet radiation by a chemical compound contained in the gas effluents, and by the optical systems being provided with ducts for admitting a cooling fluid into these systems and for cleaning their walls which are in contact with the effluent.

Measurement of the ultraviolet radiation absorption effected when the present invention is implemented can be accomplished either for the entire gas stream of which these effluents consist, or for part of this gas stream, notably by tapping off or removing a part thereof.

Figure 2:
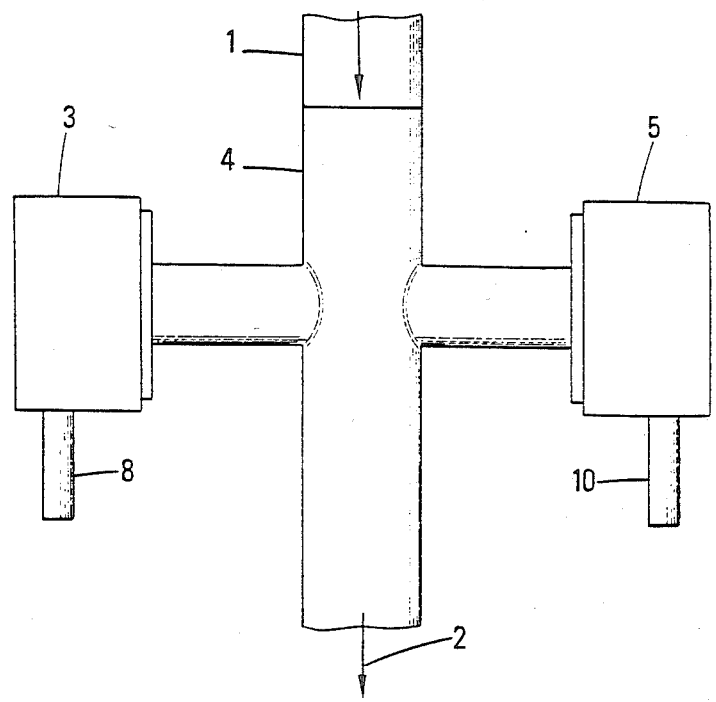
Figure 3:
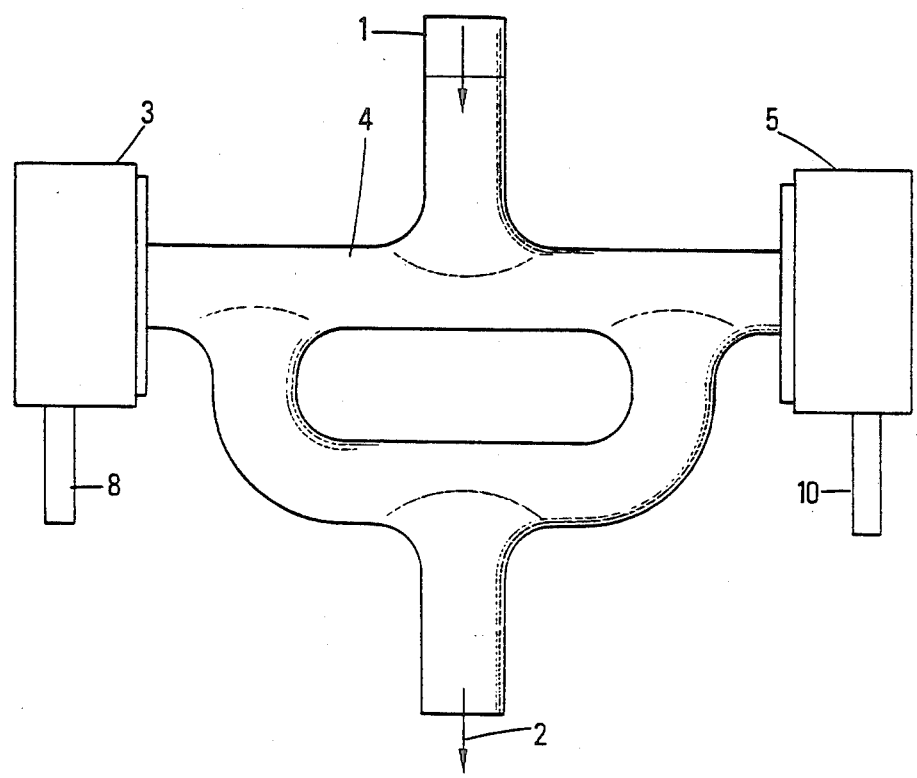
Figure 4:
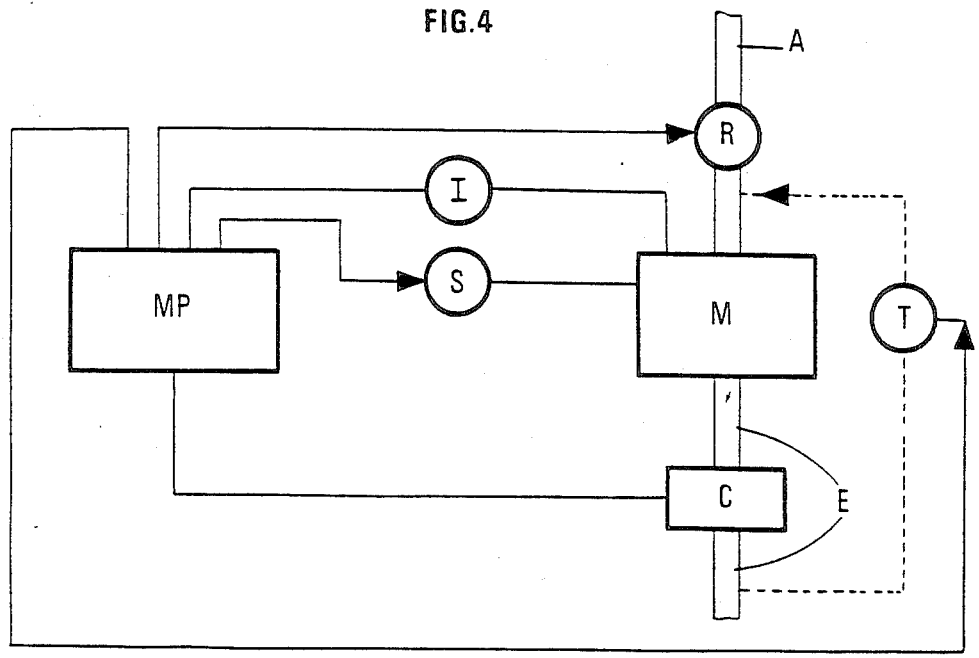

Nonlimitative embodiments of the invention are illustrated schematically by the attached drawings, wherein:

FIGS. 1–3 schematically show embodiments of the arrangement of a rapid-response device which measures the degree of absorption of ultraviolet rays by the exhaust gases of an engine (with a partial cross-section of one element being shown in FIG. 1); and FIG. 4 shows schematically an electronic assembly controlling the richness of the mixture including a device for measuring the degree of ultraviolet absorption by the exhaust gases.

As shown in FIGS. 1 to 3, elements of the devices of the invention are placed between the exhaust manifold 1 of the engine and the exhaust pipe 2, although to place the elements measuring the degree of absorption directly on the exhaust manifold to minimize the measurement response time, would not be a departure from the scope of the invention.

A first optical system 3 (shown in cross-section), emits ultraviolet radiation to a zone of small volume 4 traversed by the engine's exhaust effluents (i.e., exhaust gases) as the effluents leave the combustion chamber.

A second optical system 5, separated from the first system by zone 4, is disposed such as to receive at least part of the ultraviolet radiation which has passed through the zone 4.

Zone 4 is of very small volume to limit the period during which it is swept by the gases and, hence, the response time of the device.

The arrangements of FIGS. 1 and 3 permit a good sensitivity of the detector because the ultraviolet light is transmitted parallel to the flow of exhaust gases and thus the optical path is longer.

First optical system 3, represented schematically in cross-section in FIG. 1, comprises an ultraviolet radiation emitter source 6, e.g., a mercury argon vapor lamp, a collimator 7, and a duct 8 for admitting air or any other cleaning and cooling gas for collimator 7 in order particularly to prevent the collimator from being contaminated by contact with the exhaust gases.

The use of other means to ensure cleanliness of the optical system will not be a departure from the scope of the present invention.

Second optical system 5 has a focusing lens 9 fitted with a filter for eliminating wavelengths other than those absorbable by the "tracer" compound or compounds, e.g., a filter passing the radiations having a wavelength of 254 nanometers (this filter can also be joined to collimator 7).

A duct 10 enables air or any other gas for cleaning and cooling the focusing lense to be admitted into the second optical system.

An appropriate detection element 11, e.g., a phospho-arsenium gallium detector (GaAsP) receives the ultraviolet radiation which has passed through lens 9 and delivers an electrical signal varying with the degree to which this radiation has been absorbed by the "tracer" in the exhaust gases flowing through zone 4.

Injection of air through ducts 8 and 10 also eliminates condensation on the optical systems when starting the engine.

The temperature of systems 3 and 5 could be controlled by a thermostat with the aid of the engine cooling circuit.

For a given ultraviolet emission source, the length of the optical path through the effluents which is necessary for proper detection depends on the light current passing through these effluents, the concentration of the compound or "tracer" detected, its absorption coefficient, and the sensitivity of detector 11.

The arrangements according to FIGS. 2 and 3 have the advantage of reducing the fraction of zone 4 wherein the exhaust gases are subjected to some dilution by the cleaning and cooling fluid introduced via ducts 8 and 10. In fact, when either of the embodiments illustrated in FIGS. 2 and 3 is used, this fluid dilutes only part of the gas flow.

The volume of the zone 4 typically varies between 1 $cm^3$ and 500 $cm^3$, depending on the size of the engine.

It will be possible, without departing from the scope of the invention, to eliminate collimator 7 of system 3 from the preceding devices, retaining in system 3 only source 6 which emits ultraviolet radiation and/or to eliminate the filter from system 5, retaining therein only focusing lens 9.

The arrangement of FIG. 3 is responsive to a variation of the amount of aromatic compounds of about 25 ppm. This value is given as an example, because it depends on the sensitivity of the detector and on the size of the zone where the measurement is made.

FIG. 4 schematically represents a rapid-response detection device of the type adapted to be used with an internal-combustion engine M having an intake duct A and an exhaust pipe E and regulating elements which can be of known types and each of which is adapted to be activated by an electrical control signal.

These regulating elements can include one or more of the following elements:

regulating element R for regulating the richness of the mixture (this regulating element can, for example, alter the degree to which the air intake butterfly is open and/or the diameter of the intake flange;

valve element T such as a solenoid valve enabling the rate of recycling of the exhaust gases to be regulated in the case where the engine has a recycling line (shown in dashed lines in FIG. 4) which is traversed by a flow whose rate is a function of the degree to which valve T is open;

control element S regulating the ignition advance in the case of a controlled-ignition engine; and injection element 1 controlling the instant of injection and/or the quantity of fuel injected, in the case of a fuel-injected engine.

According to the invention, a device for detecting ultraviolet radiation absorption or sensor C (comprising optical systems 3 and 5) as heretofore described, is placed in exhaust line E, preferably as close as possible to the engine exhaust orifice or orifices.

This sensor C produces an electrical signal representing the amount of "tracer" compound (as defined above) not destroyed by combustion that exists in the exhaust gases.

The ratio between this amount and the amount of "tracer" at the intake increases when combustion becomes poor, for example, when an overly poor mixture is used, and the electrical signal from sensor C is transmitted via a calculator MP comprising, for instance, a microprocessor like the "8085 Microprocessor" sold by "Intel Corporation", to at least one of elements R, T, S, and I, such as to control these elements (in an open or closed loop) by the amount of "tracer" thus detected. This control tends to hold the amount to a minimal value.

What is claimed is:

1. A method of regulating combustion of a lean mixture by rapid-response monitoring of the gaseous effluents leaving a combustion chamber, which comprises emitting ultraviolet radiation to a zone of small volume traversed by at least part of the gaseous effluents leaving the combustion chamber, receiving at least part of the ultraviolet radiation which has passed through this zone; measuring the degree to which the ultraviolet radiation has been absorbed by a chemical compound contained in the gaseous effluents, said compound serving as an additive for detection purposes, and governing at least one parameter influencing combustion within said combustion chamber within said degree of absorption.

2. A method according to claim 1, for monitoring the gaseous effluents of an internal-combustion engine, wherein said combustion chamber is part of said internal-combustion engine and the richness of the air-fuel mixture supplied to the engine is controlled as a function of the degree of absorption of ultraviolet radiation, measured in the exhaust gases.

3. A method according to claim 1, for monitoring the gaseous effluents of an internal-combustion engine wherein said combustion chamber is part of said internal-combustion engine and the recycling rate of the exhaust gases is controlled as a function of the degree of absorption of ultraviolet radiation, measured in the exhaust gases.

4. A method according to claim 1, for monitoring the gaseous effluents of an internal-combustion engine with controlled ignition wherein said combustion chamber is part of said internal combustion engine and the engine ignition is controlled as a function of the degree of absorption of ultraviolet radiation, measured in the exhaust gases.

5. A method, according to claim 1, for monitoring the gaseous effluents of a fuel-injected internal-combustion engine, wherein said combustion chamber is part of said internal-combustion engine and the fuel injection is controlled as a function of the degree of absorption of ultraviolet radiation measured in the exhaust gases.

6. A method according to claim 1, wherein said combustion chamber is part of an internal-combustion engine and the governing of the at least one parameter influencing combustion within said combustion chamber is effected by regulating the richness of an air-fuel mixture supplied to the internal combustion engine.

7. A method of regulating combustion of a lean mixture by rapid-response monitoring of the gaseous effluents leaving a combustion chamber, which comprises adding compounds which absorb ultraviolet radiation to the fuel and/or to the combustion air before entering the combustion chamber, said compounds being normally destroyed by combustion; emitting ultraviolet radiation to a zone of small volume traversed by at least a part of the gaseous effluents leaving the combustion chamber; receiving at least a part of the ultraviolet radiation which has passed through the zone; measuring the degree to which the ultraviolet radiation has been absorbed by a chemical compound contained in the gaseous effluents and governing at least one parameter influencing combustion within said combustion chamber as a function of said degree of absorption.

8. A method of regulating combustion of a lean mixture by rapid-response monitoring of the gaseous effluents leaving a combustion chamber, which comprises adding to the fuel and/or combustion air, before entering the combustion chamber, compounds which react to a greater or lesser degree depending upon combustion quality and which furnish at least one substance with absorbs ultraviolet radiation in the exhaust gases discharged from the combustion chamber; emitting ultraviolet radiation to a zone of small volume traversed by at least part of the gaseous effluents leaving the combustion chamber; receiving at least part of the ultraviolet radiation which has passed through this zone; measuring the degree to which the ultraviolet radiation has been absorbed by a chemical compound contained in the gaseous effluents and governing at least one parameter influencing combustion within said combustion chamber as a function of said degree of absorption.

9. A method of regulating combustion of a lean mixture by rapid-response monitoring of the gaseous effluents leaving a combustion chamber, which comprises emitting ultraviolet radiation to a zone of small volume traversed by at least part of the gaseous effluents leaving the combustion chamber; receiving at least part of the ultraviolet radiation which is passed through this zone; measuring the degree to which the ultraviolet radiation has been absorbed by a chemical compound contained in the gaseous effluents, said compound serving as an additive for detection purposes, and governing at least one parameter influencing combustion within said combustion chamber as a function of said degree of absorption; the measurement of the ultraviolet radiation being carried out in a zone located in the immediate vicinity of the combustion chamber.

10. A rapid-response device enabling poor combustion of a lean mixture to be detected by monitoring the gaseous effluents leaving a combustion chamber of an internal-combustion engine, which comprises, in combination, a first optical system emitting ultraviolet radiation to a zone of small volume traversed by at least part of the effluents as the effluents leave the combustion chamber, a second optical system separated from the first optical system by said zone, said second optical system being disposed to receive at least part of the ultraviolet radiation which has traversed said zone and being associated with a means for measuring a degree of absorption of ultraviolet radiation by a chemical compound contained in the gaseous effluents, said optical systems being fitted with ducts admitting a gas for cooling said systems and for cleaning walls of the systems which are in contact with the effluents; said optical systems being disposed in contact with the engine exhaust gases in the immediate vicinity of the exhaust orifice thereof.

11. A device according to claim 10, wherein said means for measuring absorption of ultraviolet radiation is connected with means for regulating the richness of the air-fuel mixture supplied to the engine.

12. A device according to claim 10, wherein said combustion chamber is part of an internal-combustion engine, and said means for measuring absorption of ultraviolet radiation is connected to a means for regulating the recycling rate of the exhaust gases.

13. A device according to claim 10, wherein said combustion chamber is part of a controlled-ignition, internal-combustion engine and said means for measuring absorption of ultraviolet radiation is connected to means for regulating the engine ignition.

14. A device according to claim 10, wherein said combustion chamber is a fuel-injected, internal-combustion engine and said means for measuring absorption of ultraviolet radiation is connected to means for regulating the fuel injection.

15. A method of regulating combustion of a lean mixture by rapid-response monitoring of the gaseous effluents leaving a combustion chamber of an internal combustion engine which comprises introducing a fuel-air mixture containing a tracer compound, serving as an additive for detection purposes, into the combustion chamber, said tracer compound being a combustible compound that absorbs ultraviolet radiation or a combustible compound capable of producing a reaction product compound that absorbs ultraviolet radiation in case of poor combustion; emitting ultraviolet radiation to a zone of small volume traversed by at least a part of the gaseous effluents leaving the combustion chamber; receiving at least a part of the ultraviolet radiation which has passed through said zone; measuring the degree to which the ultraviolet radiation has been absorbed by a compound contained in the gaseous effluents that absorbs ultraviolet radiation and regulating at least one parameter influencing the combustion chamber as a function of the degree of absorption of the ultraviolet radiation.

* * * * *